US012758117B2

(12) United States Patent
Meeker et al.

(10) Patent No.: US 12,758,117 B2
(45) Date of Patent: Oct. 13, 2026

(54) OXYGEN SATURATION MONITORING SYSTEM

(71) Applicant: Bose Corporation, Framingham, MA (US)

(72) Inventors: David Glenn Meeker, Marlborough, MA (US); Paul David Gjeltema, Stow, MA (US); Joseph Cheah, San Diego, CA (US); Gene Ming Ko, San Diego, CA (US); Thomas John Gogg, Del Mar, CA (US); Richard Mark Wiesman, Wayland, MA (US)

(73) Assignee: Bose Corporation, Framingham, MA (US)

( * ) Notice: Subject to any disclaimer, the term of this patent is extended or adjusted under 35 U.S.C. 154(b) by 915 days.

(21) Appl. No.: 17/707,165

(22) Filed: Mar. 29, 2022

(65) Prior Publication Data

US 2023/0309854 A1 Oct. 5, 2023

(51) Int. Cl.
*A61B 5/08* (2006.01)
*A61B 5/00* (2006.01)
(Continued)

(52) U.S. Cl.
CPC .......... *A61B 5/0803* (2013.01); *A61B 5/0004* (2013.01); *A61B 5/0015* (2013.01);
(Continued)

(58) Field of Classification Search
CPC ... A61B 5/0803; A61B 5/0004; A61B 5/0015; A61B 5/024; A61B 5/14542;
(Continued)

(56) References Cited

U.S. PATENT DOCUMENTS 10,561,863 B1 * 2/2020 Dashevsky .......... A61B 5/6803
10,952,668 B2 3/2021 Ruwe et al.
(Continued)

FOREIGN PATENT DOCUMENTS

CN 112773341 A 5/2021
WO WO-2014045257 A1 * 3/2014 .......... A61B 5/0803
WO WO-2021143615 A1 * 7/2021 ......... A61B 5/14542

OTHER PUBLICATIONS

Madan A. Correlation between the levels of SpO2 and PaO2. Lung India 2017;34:307-8. (Year: 2017).*
(Continued)

*Primary Examiner* — Devin B Henson
*Assistant Examiner* — Molly Halprin
(74) *Attorney, Agent, or Firm* — Hoffman Warnick LLC

(57) ABSTRACT

Various implementations include systems and approaches for determining user oxygen saturation level, and in certain cases, performing an action based on that determination. Particular aspects include a monitoring system having at least one pressure sensor for detecting air pressure in an environment proximate the at least one pressure sensor, and a processor coupled with the at least one pressure sensor, where the processor is programmed to receive air pressure data from the pressure sensor about the environment, determine an oxygen saturation level for a user in the environment based on the air pressure data, and in response to determining the oxygen saturation level of the user has met one or more predetermined conditions, perform an action.

25 Claims, 4 Drawing Sheets

(51) Int. Cl.
*A61B 5/024* (2006.01)
*A61B 5/145* (2006.01)

(52) U.S. Cl.
CPC .......... *A61B 5/024* (2013.01); *A61B 5/14542* (2013.01); *A61B 5/7405* (2013.01); *A61B 5/742* (2013.01); *A61B 2560/0257* (2013.01); *A61B 2562/0204* (2013.01); *A61B 2562/0219* (2013.01)

(58) Field of Classification Search
CPC .................. A61B 5/7405; A61B 5/742; A61B 2560/0257; A61B 2562/0204; A61B 2562/0219
USPC .......................................................... 600/529
See application file for complete search history.

(56) References Cited

U.S. PATENT DOCUMENTS

| | | | | |
|---|---|---|---|---|
| 2015/0201873 | A1* | 7/2015 | Wilmering | A61B 5/02416 600/324 |
| 2018/0126194 | A1* | 5/2018 | Salin | A62B 7/08 |
| 2018/0192900 | A1* | 7/2018 | Wei | A61B 5/02125 |
| 2019/0090800 | A1* | 3/2019 | Bosworth | A61B 5/0015 |
| 2019/0209022 | A1* | 7/2019 | Sobol | A61B 5/681 |
| 2020/0261017 | A1* | 8/2020 | Ruwe | A61B 5/18 |

OTHER PUBLICATIONS

Dohmen et al. The effect of atmospheric pressure on oxygen saturation and dyspnea: the Tromsø study. doi.org/10.1007/s00484-020-01883-3 / Published online: Mar. 3, 2020. International Journal of Biometeorology (2020) 64:1103 (Year: 2020).*
PCT International Search Report and Written Opinion for International Application No. PCT/US2023/016688, dated Jun. 15, 2023, 12 pages.

* cited by examiner

OXYGEN SATURATION MONITORING SYSTEM

TECHNICAL FIELD

This disclosure generally relates to oxygen saturation monitoring. More particularly, the disclosure relates to approaches for non-invasive oxygen saturation monitoring based at least partially on air pressure measurement.

BACKGROUND

Oxygen saturation monitoring and air quality monitoring (e.g., for dangerous air-quality scenarios) are significant considerations in certain industries (e.g., aviation, industrial work environments, etc.). Additionally, dangerous air-quality scenarios are significant considerations in any enclosed space. However, conventional approaches for monitoring user oxygen saturation are inaccurate, unwieldy, and/or power hungry. Further, conventional air quality monitoring does not account for user health risks related to oxygen saturation, providing an incomplete picture of the user's current health condition.

SUMMARY

All examples and features mentioned below can be combined in any technically possible way.

Various implementations include systems and approaches for determining user oxygen saturation level, and in certain cases, performing an action based on that determination. Additional implementations include a wearable audio device configured to monitor user oxygen saturation level.

In some particular aspects a monitoring system includes: at least one pressure sensor for detecting air pressure in an environment proximate the at least one pressure sensor; and a processor coupled with the at least one pressure sensor, where the processor is programmed to receive air pressure data from the pressure sensor about the environment, determine an oxygen saturation level for a user in the environment based on the air pressure data, and in response to determining the oxygen saturation level of the user has met one or more predetermined conditions, perform an action.

In other particular aspects, a method of monitoring an oxygen saturation level of a user includes: receiving air pressure data from at least one pressure sensor about an environment proximate the at least one pressure sensor; determining an oxygen saturation level for the user in the environment based on the air pressure data, and in response to determining the oxygen saturation level of the user has met one or more predetermined conditions, performing an action.

In additional particular aspects, a wearable audio device includes: an electro-acoustic transducer for providing an audio output; a microphone; a pressure sensor for detecting air pressure in an environment proximate the wearable audio device; and a processor coupled with the pressure sensor, the microphone, and the electro-acoustic transducer, where the processor is programmed to receive at least one user characteristic about a user of the wearable audio device, receive air pressure data from the pressure sensor about the environment, and determine an oxygen saturation level for the user based on the at least one user characteristic and the air pressure data.

Implementations may include one of the following features, or any combination thereof.

In certain cases, the oxygen saturation level is determined using a physiology model having an oxygen saturation level correspondence with air pressure data.

In particular aspects, the physiology model has a variable sensitivity based on at least one environmental gaseous mixture characteristic.

In certain cases, environmental gaseous mixture characteristics include: detected air pressure, altitude, a carbon monoxide value, or a nitrogen value.

In some implementations, the physiology model further includes an oxygen saturation level correspondence with user characteristics, and determining the oxygen saturation level includes: applying a first weight to the air pressure data based on a first value for a first user characteristic; and applying a second weight to the air pressure data based on a second value for the first user characteristic, where the first weighted air pressure results in a first determined oxygen saturation level and the second weighted air pressure results in a second determined oxygen saturation level.

In certain aspects, the first user characteristic includes gender, and the first value is a default gender value.

In particular cases, if one of the predetermined conditions includes determining that the oxygen saturation level deviates from an oxygen saturation threshold, the processor is further configured to take a first corrective action.

In some implementations, the system further includes a carbon monoxide sensor coupled with the processor for providing a carbon monoxide measurement about the environment.

In some aspects, the carbon monoxide measurement enhances an accuracy of the determined oxygen saturation level.

In particular implementations, if the carbon monoxide measurement indicates a carbon monoxide level exceeding a threshold, the processor is further configured to take a second, distinct corrective action.

In certain aspects, the processor is further programmed to provide a notification to the user to select at least one individual user characteristic prior to determining an oxygen saturation level for the user, where the notification indicates that the at least one individual user characteristic enhances accuracy in determining the oxygen saturation level for the user.

In some cases, the processor is further programmed to determine the oxygen saturation level based on at least one user characteristic, where the at least one user characteristic includes one or more of: gender, resting heart rate, age, weight, resting respiration rate, or baseline blood pressure.

In particular aspects, the at least one user characteristic is selected by the user or all of the user characteristics are default user characteristics.

In certain implementations, the at least one user characteristic is received from a physiological sensor in the environment.

In some aspects, the system further includes: a wearable audio device coupled with the processor, where the wearable audio device includes the physiological sensor.

In particular cases, the physiological sensor includes an optical sensor for providing eye movement data for use by an action decision model.

In some aspects, the oxygen saturation level includes at least one of an arterial blood gas level or a pulse oxygen level.

In certain implementations, the system further includes at least one additional sensor for providing an input that impacts the determined oxygen saturation level or whether to perform the action, the at least one additional sensor including one or more of: an oxygen sensor, a carbon monoxide sensor, an inertial measurement unit, an optical sensor, or a microphone.

In particular cases, the at least one additional sensor includes a set of redundant sensors at physically distinct devices.

In some aspects, the system further includes: a wearable audio device coupled with the processor, the wearable audio device including at least one electro-acoustic transducer for providing an audio output and at least one microphone, wherein the processor is configured to: prompt the user to speak, receive voice signals from the user after the prompt, and identify a potential oxygen saturation level indicator based on the received voice signals, or monitor voice signals from the user over a period, and identify a potential oxygen saturation level indicator based on the monitored voice signals.

In certain implementations, the wearable audio device includes an aviation headset, and the processor is at least partially contained in the wearable audio device or an electronic flight bag coupled with the wearable audio device.

In some cases, the wearable audio device includes a set of in-ear earpieces.

In particular aspects, the system further includes an oxygen sensor coupled with the processor for providing an indicator of at least one of an oxygen level or a nitrogen level in the environment.

In some cases, the processor is further configured to: provide feedback to the user to adjust the determined oxygen saturation level in response to the determined oxygen saturation level deviating from a threshold.

In certain implementations, the action includes at least one of: providing feedback to the user about one of the predetermined conditions, alerting another user about one of the predetermined conditions, or automatically taking a corrective action.

In some aspects, an aviation headset includes the wearable audio device, and further includes at least one additional sensor for providing an input that impacts the determined oxygen saturation level or whether to perform the action, the at least one additional sensor including one or more of: an oxygen sensor, a carbon monoxide sensor, an inertial measurement unit, or an optical sensor.

Two or more features described in this disclosure, including those described in this summary section, may be combined to form implementations not specifically described herein.

The details of one or more implementations are set forth in the accompanying drawings and the description below. Other features, objects and advantages will be apparent from the description and drawings, and from the claims.

Figure 1:
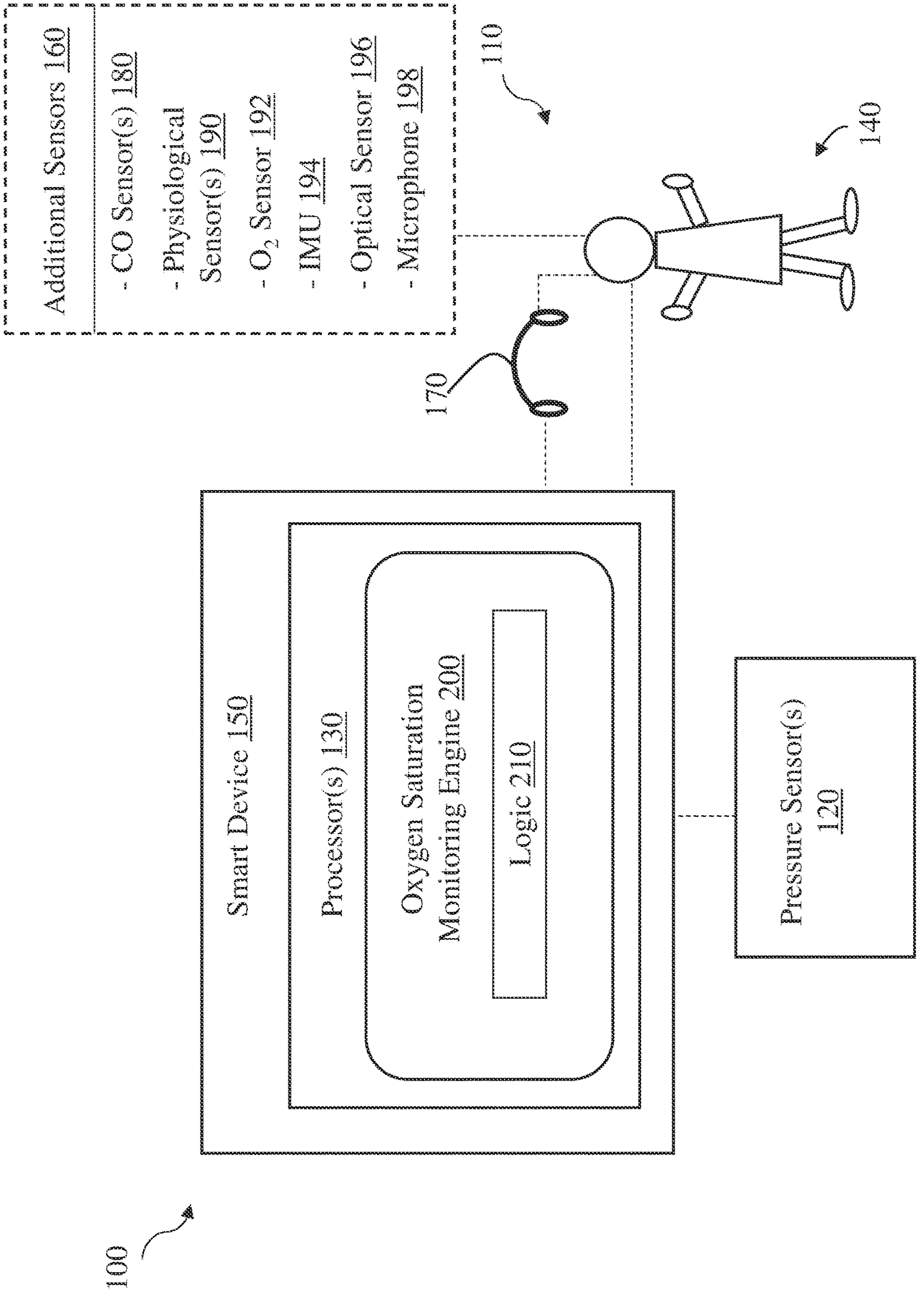
FIG. 1 is a schematic diagram illustrating components in an environment according to various implementations.

It is noted that the drawings of the various implementations are not necessarily to scale. The drawings are intended to depict only typical aspects of the disclosure, and therefore should not be considered as limiting the scope of the implementations. In the drawings, like numbering represents like elements between the drawings.

DETAILED DESCRIPTION

This disclosure is based, at least in part, on the realization that user oxygen saturation level can be monitored using a variety of non-physiological criteria to aid in safety, situational awareness, and/or fatigue mitigation. For example, a system can use air pressure data and a physiology model to determine an oxygen saturation level for a user, and in some cases, perform an action based on the determined oxygen saturation level.

Commonly labeled components in the FIGURES are considered to be substantially equivalent components for the purposes of illustration, and redundant discussion of those components is omitted for clarity.

Poor environmental (e.g., air) quality, particularly in enclosed spaces, can have significant negative health impacts. People in a variety of environments and/or occupations can benefit from accurate and timely monitoring of environmental conditions such as characteristics of the air they breathe. For example, vehicle operators and/or passengers, aircraft pilots and/or passengers, industrial workers (e.g., handling sensitive chemicals, or in clean rooms), operators and/or passengers of maritime equipment, etc., benefit from knowing that their environmental conditions are not negatively impacting their health. A particular health condition of concern to many of these users is hypoxia, otherwise known as a low oxygen saturation level. Hypoxia can manifest in a number of significant and undesirable ways, including shortness of breath, rapid pulse, localized pain, syncope, mental disturbances, etc.

Conventional approaches for monitoring air quality and characteristics in environments of risk (e.g., for aircraft pilots, maritime vessel operators, or industrial workers) are prone to inaccuracy and/or ineffectiveness. Conventional sensing performed in such environments is aimed at providing warnings to users about dangerous contaminants (e.g., carbon monoxide or nitrogen). These conventional approaches do not provide additional, significant information such as user health characteristics and/or environmental conditions impacting such characteristics. For example, conventional monitoring systems in environments of risk do not assess or monitor the pulse oxygen level of users. Additionally, conventional pulse oximeters such as those used in the health care industry have a number of drawbacks including: inaccuracies in detecting oxygen saturation in the presence of carbon monoxide, sensitivity to motion (e.g., G-forces) and variations in skin color, high power consumption, and logistical challenges integrating such oximeters into wearable devices such as headsets and/or wearable audio devices.

In contrast to conventional approaches, various implementations include a system having one or more pressure sensors and a processor coupled with the pressure sensor(s) and configured to determine an oxygen saturation level for a given user in an environment based on the air pressure data and a user physiology model. In certain cases, such as where the oxygen saturation level meets one or more predetermined conditions (e.g., indicating hypoxia or another health risk), the processor performs an action (e.g., issuing a warning, recommended user action, and/or taking a proactive corrective action to mitigate the environmental risk). The processor accesses a physiology model that has air pressure to oxygen saturation level correspondence for a given user or user characteristics. In some cases, the user characteristic(s) include default user characteristic(s). In other cases, at least one of the user characteristics is selected by the user or received from a physiological sensor in the environment. In any case, the monitoring system is configured to determine an oxygen saturation level for a user in an environment based on a sensed air pressure in the environment, and in certain cases, based on the oxygen saturation level, perform an action.

FIG. 1 shows a schematic depiction of data flows in an environment 100 including a monitoring system 110 according to various implementations. In some examples, the environment 100 can include the cabin of a vehicle such as an aircraft, a maritime vehicle, a public transport vehicle, a construction vehicle, etc. However, in various additional implementations, the environment 100 can include the cabin or control room of any vehicle. Additionally, the environment 100 can include any enclosed space such as an industrial work environment, a clean room, an office space, a residential space, etc. The monitoring system 110 is shown including at least one pressure sensor 120 for detecting the pressure in environment 100, and a processor 130 coupled with the pressure sensor 120 for determining an oxygen saturation level for a user 140 in the environment 100. In certain cases, the processor 130 resides on, or otherwise executes functions at, a smart device 150. In other cases, the processor 130 can be physically located at one or more computing devices and perform functions described herein. In certain optional cases (depicted in phantom), the monitoring system 110 can include at least one additional sensor 160 coupled with the processor 130, e.g., for providing data about the environment 100 and/or the user 140. In particular optional examples, the pressure sensor(s) 120, processor 130 and/or additional sensor(s) 160 are physically co-located in a given device, e.g., a smart device 150. In other cases, the pressure sensor(s) 120, processor 130 and/or additional sensor(s) 160 are located at distinct devices. In a particular example, a wearable device 170 such as a wearable audio device like a headset integrates one or more of the pressure sensor(s) 120, processor 130 and/or additional sensor(s) 160. In example implementations where the environment 100 is an aircraft (e.g., aircraft cockpit), the smart device 150 can be connected with a flight management system that is configured to manage flight conditions according to the prescribed flight pattern.

In various implementations, the additional sensors 160 are configured to detect additional environmental characteristics in the environment 100 and/or physiological characteristics about the user 140 in the environment 100. For example, the additional sensors 160 can include a carbon monoxide sensor 180 for detecting the presence of carbon monoxide in the environment 100. Additional sensors 160 can also include one or more physiological sensor(s) 190 configured to detect physiological conditions about the user 140. In some cases, the physiological sensor(s) 190 are located in the wearable device 170, at the smart device 150 or in another piece of hardware proximate the user 140 in the environment 100 (e.g., in a seat, armrest, control apparatus, dashboard, user interface, windshield, etc.). In various implementations, the physiological sensors 190 can include one or more biometric sensors such as a heart rate sensor, a photoplethysmogram (PPG), electroencephalogram (EEG), electrocardiogram (ECG) or EGO) optical/laser-based sensors and/or vision systems for tracking movement or speed, light sensors for detecting time of day, audio sensors (e.g., microphones) for detecting human or other user speech or ambient noise, electrodermal activity (EDA) sensors for detecting electrodermal activity of the pilot, etc. In additional cases, the physiological sensors 190 can include or utilize an inertial measurement unit (IMU) and/or a global positioning system (GPS) to detect user movement. In particular cases, the physiological sensors 190 are configured to gather physiological condition data including one or more of: a heart rate of the user 140, a heart rate variability of the user 140, an electrical activity from the brain of the user 140, an electrical activity from the heart of the user 140, a respiration rate of the user 140, electrodermal activity of the user 140, eye movement of the user 140, or body movement and/or position change of the user 140.

As described further herein, the additional sensors 160 can provide an input that impacts the determined oxygen saturation level and/or whether to take a prescribed action. In addition to, or including the CO sensor(s) 180 and the physiological sensor(s) 190, the additional sensors 160 include an oxygen ($O_2$) sensor 192, an inertial measurement unit (IMU) 194, an optical sensor 196 (e.g., for sensing and/or tracking eye movement, facial movement and/or facial expression) and/or a microphone 198 (which may be separate, or redundant sensors relative to the group of physiological sensors 190, used to pick up human speech, e.g., for detecting hypoxia and/or other physiological conditions manifesting in detectable speech pattern). For example, the IMU 194 can track head movement and/or overall body movement of the user 140 as an input, e.g., for hypoxia determination. In such cases, erratic head and/or body movement, or lethargic head and/or body movement by the user 140 can provide a significant input for the monitoring engine 200 in detecting hypoxia. In certain cases, the optical sensor 196 can be used for detecting eye movement and/or detecting movement of the user's head and/or body in a similar manner as the IMU 194. As described herein, the microphone(s) 198 can be part of a wearable (e.g., audio) device such as wearable device 170, or can include a separate microphone or microphone array. In certain cases, the microphone(s) 198 are configured to aid in speech analysis for detecting medical conditions, e.g., via indicators such as hypoxia, carbon monoxide-induced hypoxia, etc. In certain cases, sensors that directly impact the oxygen saturation level calculation include air pressure sensor(s), carbon monoxide sensor(s) and oxygen sensor(s). The IMU and/or optical sensors may provide indicators of events that may occur as a result of abnormal physiological conditions, for example, in assessing whether to take a prescribed action.

In certain implementations, the additional sensor(s) 160 can include one or more redundant sensors at physically distinct devices, e.g., sensors at the smart device 150 and the wearable device 170, or sensors at two or more of: the smart device 150, wearable device 170, an electronic flight bag, or a vehicle (e.g., aircraft) interface. In some cases, two or more pressure sensors 120 are located at physically distinct devices. In particular aspects, redundant sensors such as pressure sensors 120, CO sensors 180, or optical sensors 196 at physically distinct devices can enhance the accuracy of measurements inputs from those sensors to the monitoring engine 200, e.g., where the monitoring engine 200 is configured to average, scale or otherwise weight inputs from redundant sensors providing distinct input values. Additionally, the redundant sensors can prevent false triggers, e.g., for carbon monoxide or pressure, based on a faulty sensor and/or a measurement error from one or more sensors.

The monitoring system 110 can include at least one computing system (including one or more processors, memory, control circuits, user interface(s), etc.) as well as a communications system (e.g. one or more wireless transceivers, satellite communication/navigation systems, etc.). In cases where the monitoring system 110 is part of a vehicle, aircraft or maritime operator monitoring system (e.g., a pilot monitoring system), the monitoring system 110 can be configured to maintain communication with one or more communication networks, e.g., air traffic control towers. In certain implementations, the monitoring system 110 is integrated with, or otherwise communicates with a control system for a vehicle, aircraft, maritime vessel, etc., to manage configuration settings (e.g., auto-pilot and other in-operation control features), obtain travel condition data from one or more sensors, and/or manage the travel route.

In some cases, the smart device 150 includes an electronic flight bag. In other cases, the smart device 150 can include one or more personal computing devices (e.g., desktop or laptop computer), wearable smart devices (e.g., smart watch, smart glasses), a smart phone, a tablet, or a remote control device. Smart device 150 can include a conventional user interface for permitting interaction with a user, and can include one or more network interfaces for interacting with the pressure sensor(s) 120, additional sensors 160, a wearable device 170, and other components in the environment 100 (e.g., a vehicle management system such as a flight management system). Smart device 150 can further include embedded sensors for measuring biometric information about user, e.g., body temperature; heart rate; or movement patterns (e.g., via accelerometer(s)). In additional implementations, smart device 150 can access physiological information about the user 140 from a locally executed application or an application on another smart device (e.g., the pilot's smart watch, smart phone, exercise watch, etc.). For example, the smart device 150 can access physiological information about the user's sleep patterns, duration of sleep, activity level, resting heart rate, etc., as tracked by one or more applications running on the smart device 150 or another smart device that is connected with the smart device 150.

The smart device 150 is configured to perform processes to monitor the oxygen saturation of the user 140 according to various implementations. In various implementations, the smart device 150 includes processor 130 for executing functions in oxygen saturation monitoring as described herein. The processor 130 may include a plurality of processors, implemented for example as a chipset of chips that include separate and multiple processors, e.g., analog and digital processors. The processor(s) 130 may provide, for example, for coordination of other components of the smart device 150, such as control of user interfaces (not shown) and applications run by the smart device 150. The processor(s) 130 can be coupled with or otherwise be integrated with memory that maintains (e.g., stores) or otherwise accesses an oxygen saturation monitoring engine 200, which is run by the processor 130. The oxygen saturation monitoring engine 200 can include logic 210 for executing functions described herein. In some cases, the oxygen saturation monitoring engine (or, "monitoring engine") 200 includes a software application such as a mobile device application that is configured perform functions in monitoring the oxygen saturation of the user 140.

Figure 2:
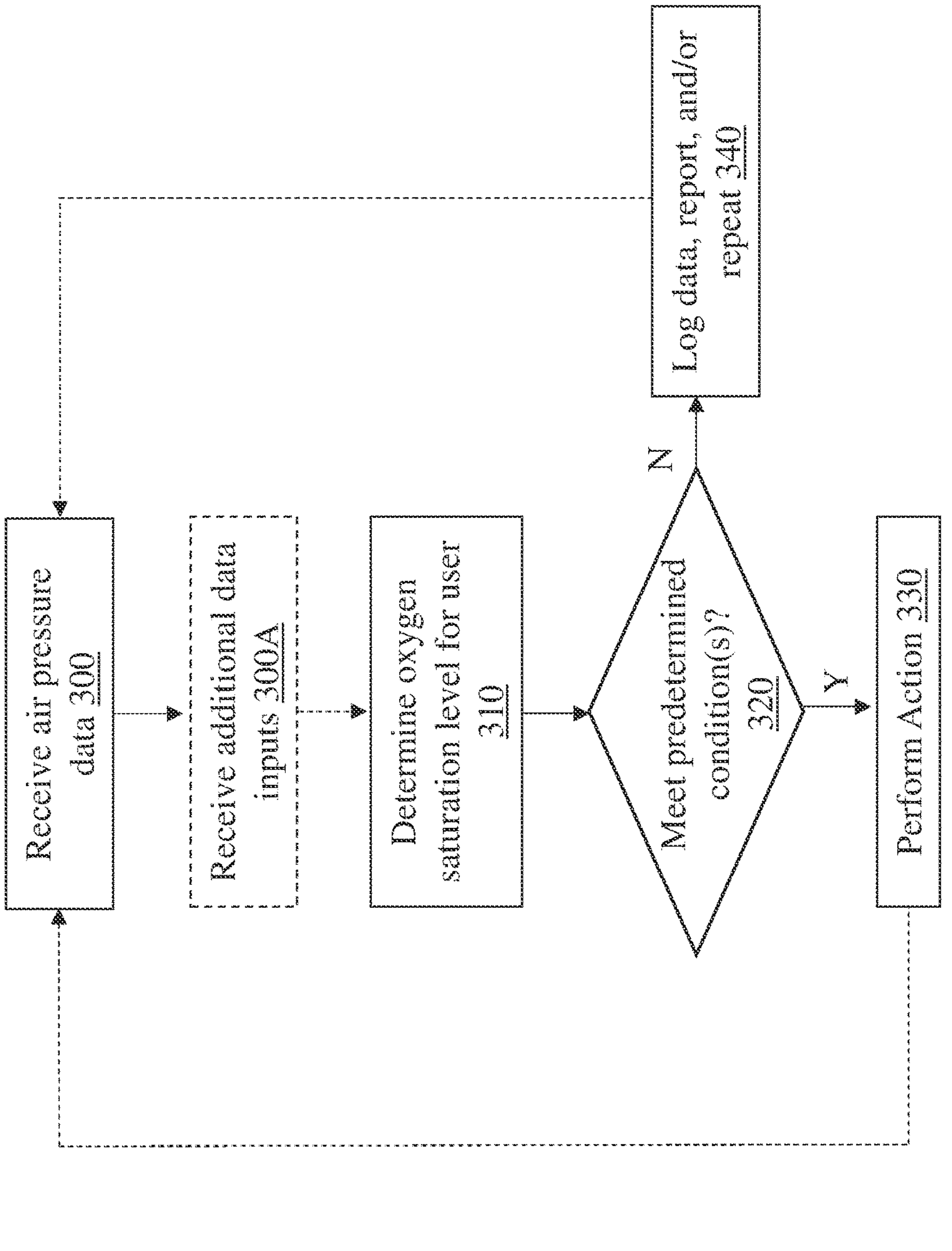
FIG. 2 is a process flow diagram illustrating processes performed by an oxygen saturation monitoring engine as shown in the environment of FIG. 1.

FIG. 2 is a flow diagram illustrating processes performed by the monitoring engine 200 according to various implementations. With reference to both FIG. 1 and FIG. 2, in various implementations, the monitoring engine 200 is configured to receive and analyze data from one or more systems and devices in the environment 100. As shown in FIG. 2, the monitoring engine 200 is configured to receive air pressure data (process 300) about the environment 100 from the pressure sensor 120. The monitoring engine 200 is further configured to determine an oxygen saturation level for the user 140 in the environment 100 based on the air pressure data from sensor 120 (process 310). The monitoring engine 200 is further configured to compare the determined oxygen saturation level with one or more predetermined condition thresholds (decision 320). In response to determining that the oxygen saturation level satisfies at least one of the predetermined condition thresholds (Yes to decision 320), the monitoring engine 200 performs an action (process 330). If the oxygen saturation level does not satisfy any of the predetermined condition thresholds (No to decision 320), in process 340 the monitoring engine 200 can log the oxygen saturation level data, repeat one or more processes (e.g., processes 300-320), and/or provide the oxygen saturation level data in a report. It is understood that the monitoring processes described herein can be repeated on a periodic, continuous, or on-demand basis, and in certain cases, the monitoring engine 200 will repeat one or more processes (e.g., process 300 to process 330 or process 340), as indicated by dashed arrows in FIG. 2. In some additional implementations, the monitoring engine 200 is configured to receive additional sensor inputs and/or user characteristic data for use in determining oxygen saturation level for the user 140. For example, additional sensor inputs and/or user characteristic data can include carbon monoxide level data from CO sensor(s) 180 and/or physiological condition data from the physiological sensors 190, and perform additional actions. This process is illustrated as process 300A in phantom as optional, the details of which are described further herein.

In various implementations, the monitoring engine 200 receives the pressure data (from pressure sensor(s) 120) and additional data (from additional sensors 160) on a continuous basis, however, in some cases, this data is received on a periodic basis. In some cases, the monitoring engine 200 can be configured to receive this pressure data (and in some cases, CO data and/or physiological condition data) during operation of a vehicle, e.g., during an aircraft flight.

In some particular implementations, the predetermined condition threshold includes multiple thresholds, for example, a first (e.g. higher oxygen saturation level) threshold that corresponds with a caution indicator, a second (e.g., relatively lower oxygen saturation level) that corresponds with a warning or preventative action indicator, and a third (e.g., low, or minimum oxygen saturation level) that corresponds with a corrective action indicator. Corrective actions can include, for example, providing feedback to the user 140 about the predetermined condition (e.g., low oxygen saturation level approaching a risk level) such as via an interface at the smart device 150 and/or in a control system coupled with the smart device 150 (e.g., flight control system, vehicle interface, etc.). As noted herein, interface feedback can include one or more of audio feedback such as via a transducer in the smart device 150 and/or the wearable device 170, haptic feedback such as a vibrational pattern delivered at the smart device 150 and/or the wearable device 170, and/or visual feedback at smart device 150 and/or an interface in the vehicle. Additional corrective actions can include alerting another user (e.g., copilot, air traffic control, co-operator) about one of the predetermined conditions (e.g., hypoxia warning), and/or automatically taking a corrective action. In corrective action scenarios, the monitoring engine 200 is configured to switch an operating mode in a vehicle or aircraft into an autopilot/auto-controller mode.

Figure 3:
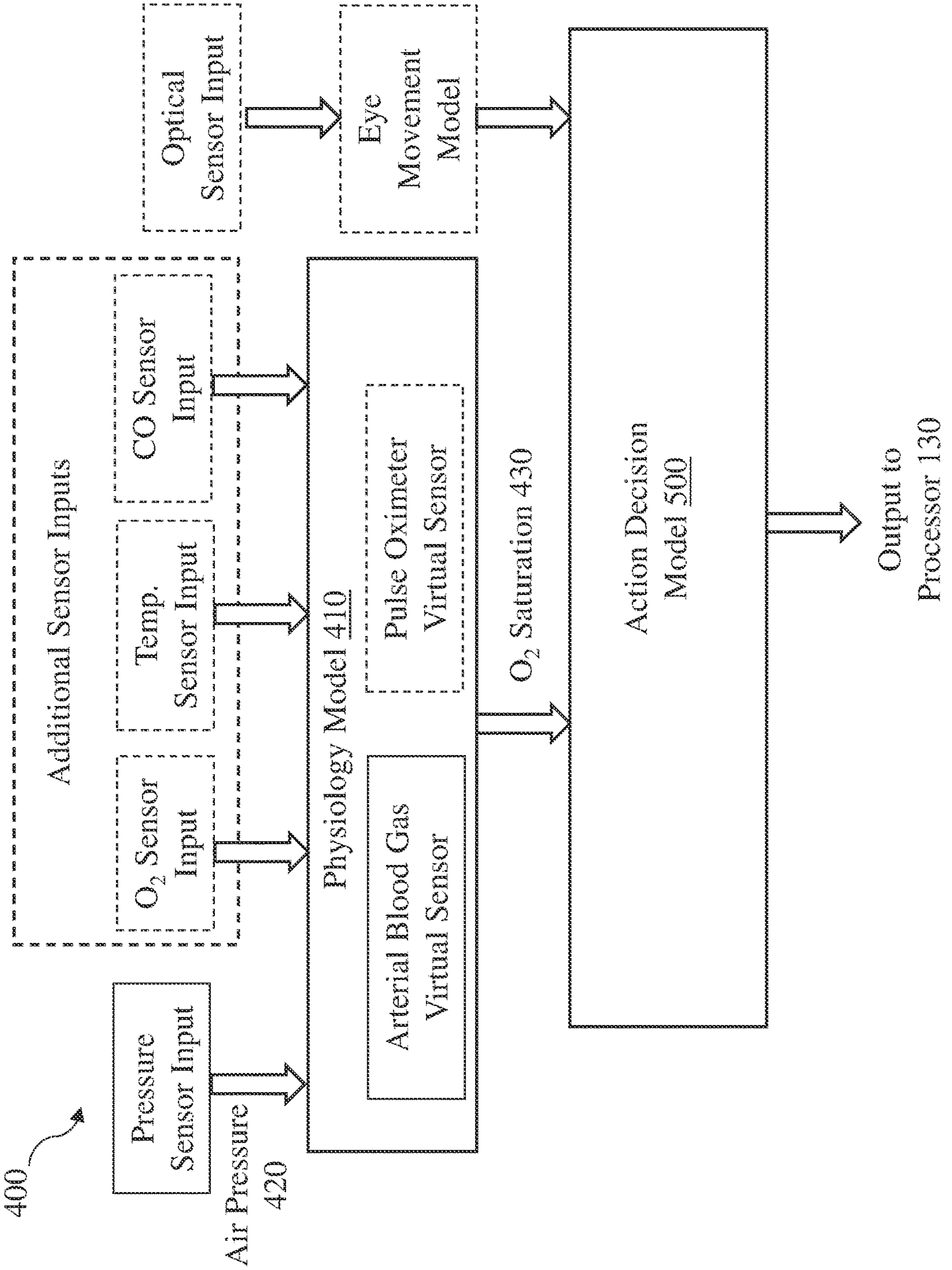
FIG. 3 is data flow diagram illustrating control processes performed by an oxygen saturation monitoring engine according to various implementations.
Figure 4:
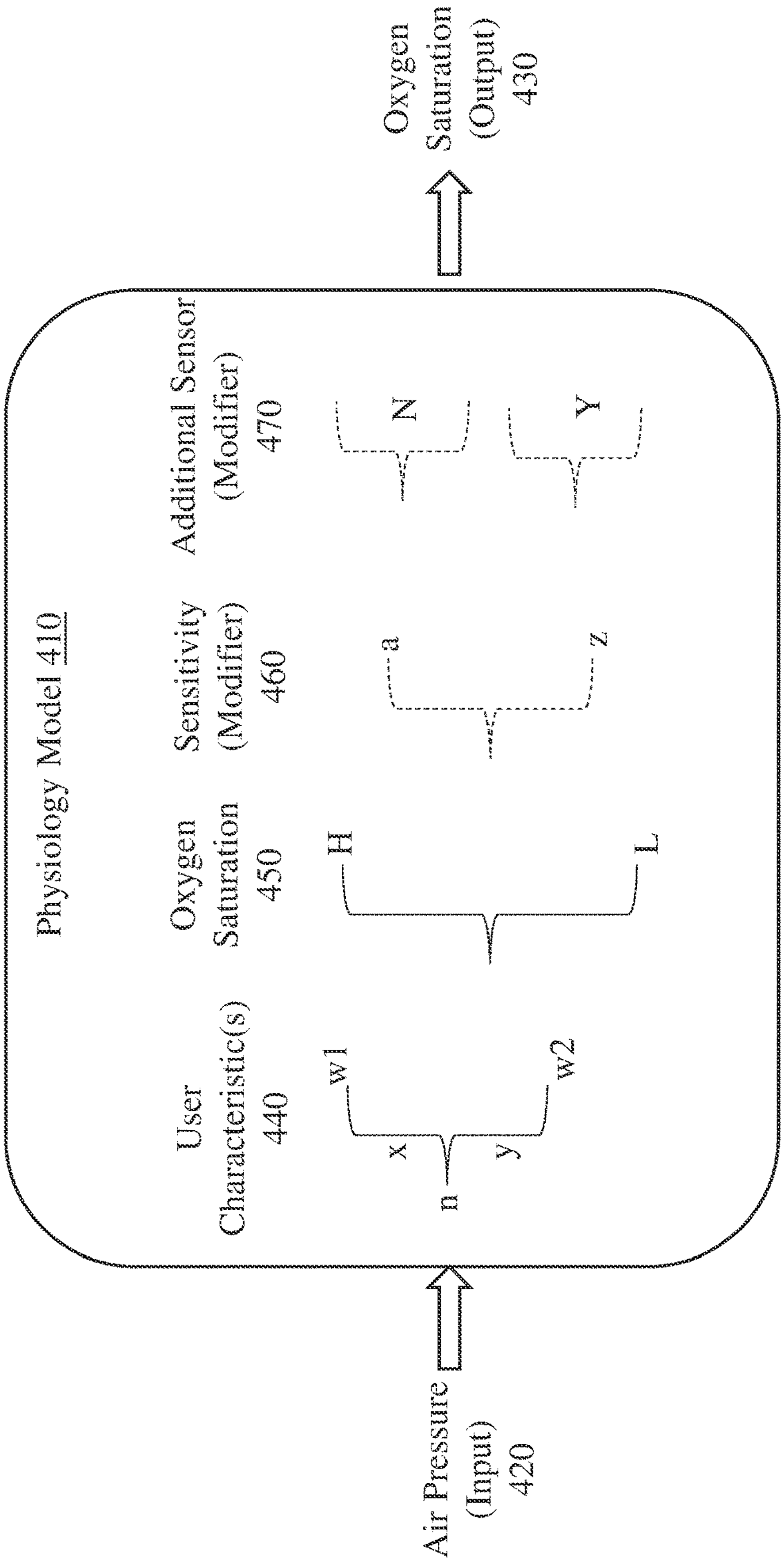
FIG. 4 is a data flow diagram illustrating features in the physiology model within the oxygen saturation monitoring engine according to various implementations.

In various implementations, as illustrated in the data flow diagram 400 in FIG. 3, the oxygen saturation level of the user 140 can be determined using a physiology model 410 having an air pressure data 420 correspondence with oxygen saturation level 430. In certain cases, the physiology model 410 includes a set of digital engines including logic for calculating blood oxygen saturation: an arterial blood gas virtual sensor and, optionally, a pulse oximeter virtual sensor. That is, in various implementations the determined oxygen saturation level includes at least one of an arterial blood gas level or a pulse oxygen level. In particular cases, the determined oxygen saturation level includes at least an arterial blood gas level. FIG. 4 shows a simplified example of the physiology model 410, illustrating air pressure data 420 as an input and oxygen saturation as an output 430. With reference to FIGS. 3 and 4, in various implementations, the physiological model 410 benefits from both directly measured inputs such as air pressure, as well as inferred inputs, such as user characteristics (e.g., gender, height/weight, resting blood pressure, etc.). In cases where the monitoring engine 200 is used in conjunction with a vehicle or aircraft trip (flight) management system, the physiology model 410 can also account for trip profiles, e.g., flight profiles based on historical flight data. In these cases, the trip profiles can be based on a regressive analysis of usage (e.g., flight or other trip) data such as direct oxygen measurement data. For example, the correspondence(s) in the physiology model 410 can be based on direct blood oxygen measurement (e.g., using a pulse oximeter) of users in a set of trips (e.g., flights), along with air pressure data and user characteristic data about the users.

In various implementations, the physiology model includes an oxygen saturation level correspondence with user characteristics 440. In certain cases, determining the oxygen saturation level 430 includes applying a first weight (w1) to air pressure data 420 based on a first value for a first user characteristic 440, and applying a second weight (w2) to air pressure data 420 based on a second value for the first user characteristic 440. As illustrated in FIG. 4, a given user characteristic (n) can have at least two values (e.g., x and y), associated with distinct weights (w1, w2) to be applied to the air pressure data 420. In some cases, user characteristics can have a range of values, e.g., a numerical range or a set of values. In particular cases, the user characteristic includes gender, e.g., male or female. In some cases, the model 410 includes a default gender value, such that the user 140 need not provide information about his/her gender for the model 410 to determine an oxygen saturation level 430 based on the detected air pressure 420. In particular aspects, the default gender value is male, i.e., male gender. In these cases, without a specific gender input value about the user 140, the model 410 is configured to determine the oxygen saturation level 430 based on measured air pressure data 420 and the inferred (default) user characteristic 440 of a male user 140. Based on the weight (w1, w2, etc.) applied to the air pressure data 420, a preliminary oxygen saturation value 450, or range of values is determined. In some cases, the preliminary oxygen saturation value/range 450 is on a range, between a high (H) value and a low (L) value. In particular implementations, a preliminary oxygen saturation value 450 at or near the low value (L) indicates a high-risk oxygen saturation situation for the user 140. For example, a preliminary oxygen saturation value 450 below a midpoint in the high-low range presents at least some risk of hypoxia, while an oxygen saturation value 450 in the lower third, quartile, or decile of the high-low range can be associated with an even higher risk of hypoxia.

While gender is described as one of the user characteristics 440, various alternative, or additional user characteristics 440 can be used to adjust (e.g., apply weight(s) to) the measured air pressure 420 in order to determine oxygen saturation. For example, additional user characteristics 440 about the user 140 can include: i) resting heart rate, ii) age, iii) weight, iv) resting respiration rate, or v) baseline blood pressure. In certain cases, the user 140 can select (e.g., via an interface) or otherwise provide (e.g., via a health profile) one or more of the user characteristic(s) 440 to the oxygen saturation monitoring engine 200. In additional cases, at least one of the user characteristic(s) 440 is a default characteristic (e.g., a default gender and baseline blood pressure range).

In still further implementations, the user characteristic(s) 440 is received from one or more of the physiological sensor(s) 190 in the environment 100 (FIG. 1). For example, the physiological sensor 190 can include an optical sensor for providing eye movement data about the user 140. In certain cases, the optical sensor can include a vision-based sensor, with a programmed routine that looks at eye motion and degree of pupil dilation and/or movement.

In certain implementations, the processor 130 is programmed to provide a notification to the user 140 (e.g., via any interface described herein) to select at least one individual user characteristic prior to determining an oxygen saturation level for the user 140. In some cases, the notification indicates that the user characteristic(s) from which the user 140 can select will enhance accuracy in determining the oxygen saturation level for the user 140. For example, the notification can include a text-based notification or an audible notification indicating to the user that selecting one or more characteristics will enhance accuracy in determining oxygen saturation level for the user 140.

According to certain implementations, the additional sensor(s) 160 can be used to provide user characteristic(s) 440 about the user 140, e.g., for applying one or more weights to the air pressure data 420 to aid in determining the preliminary oxygen saturation level 450. However, in an optional configuration, the additional sensors 160 can also be used to modify the sensitivity of the physiology model 410, e.g., to increase or decrease the sensitivity of the model 410 in calculating the oxygen saturation level output 430. For example, the model 410 can include a sensitivity modifier 460 that modifies the sensitivity of the determined oxygen saturation level 450 based on at least one measurement or determined input from the additional sensors 160 deviating from a threshold. For example, the model 410 can have a variable sensitivity based on an environmental gaseous mixture characteristic (e.g., applied as sensitivity modifier 460). In certain cases, environmental gaseous mixture characteristics include detected air pressure, altitude, a carbon monoxide value, or a nitrogen value. In certain cases, one or more of the environmental gaseous mixture characteristics is inferred or set as a default value. In additional cases, one or more environmental gaseous mixture characteristics is estimated or inferred from another environmental gaseous mixture characteristic, e.g., air pressure estimated based on altitude, and vice versa. In a particular example, air pressure can be correlated with altitude (and vice versa) in an unpressurized aircraft cabin. In a particular implementation, the sensitivity modifier 460 is applied based on at least one of: a) the detected air pressure in environment 100 deviating from a threshold pressure, b) an altitude value (e.g., measurement or inferred value) of the environment 100 deviating from a threshold altitude, c) a carbon monoxide value (e.g., measurement or inferred value) of the environment 100 deviating from a threshold carbon monoxide level, or d) a nitrogen value (e.g. measurement or inferred value) of the environment 100 deviating from a threshold nitrogen level. For example, a high pressure environment indicated by an air pressure value 420 that exceeds a high pressure threshold can increase the sensitivity of the model 410 to a preliminary oxygen saturation level 450 that deviates from an oxygen saturation level threshold (e.g., determined oxygen saturation is below a desired level for the user 140). Additionally, or alternatively, a low pressure environment indicated by an air pressure value 420 below a low pressure threshold can increase the sensitivity of the model 410 to a preliminary oxygen saturation level 450 that deviates from an oxygen saturation level threshold (e.g., determined oxygen saturation is below a desired level for the user 140). In another example, a high altitude environment indicated by an altitude measurement from an additional sensor 160 (e.g., altitude sensor) that exceeds a high altitude threshold can increase the sensitivity of the model 410 to a preliminary oxygen saturation level 450 that deviates from an oxygen saturation level threshold (e.g., determined oxygen saturation is below a desired level for the user 140). Additionally, or alternatively, a low altitude environment indicated by an altitude measurement from an additional sensor 160 (e.g., altitude sensor) below a low altitude threshold can increase the sensitivity of the model 410 to a preliminary oxygen saturation level 450 that deviates from an oxygen saturation level threshold (e.g., determined oxygen saturation is below a desired level for the user 140).

As further illustrated in FIG. 4, in an optional configuration, the model 410 can also include an additional sensor modifier 470 for adjusting the determined preliminary oxygen saturation level 450. In these cases, the additional sensor modifier 470 adjusts the determined preliminary oxygen saturation level 450 based on an input from one or more of the additional sensors 160. While the sensitivity modifier 460 can be used to adjust the sensitivity (e.g., variation) in the determined oxygen saturation level 450, the additional sensor modifier 470 can be used as a threshold mechanism to trigger an adjustment to the oxygen saturation level 450 or provide an additional reason to trigger a health-related concern for the user 140. For example, the oxygen sensor 192 can be configured to provide an indicator of the oxygen level in the environment 100. Additionally, the indicator of the oxygen level in the environment 100 can be used to derive a nitrogen level and/or a CO level in the environment 100. In certain cases, if the oxygen sensor 192 indicates a low oxygen environment (e.g., detected oxygen level is below a threshold), the model 410 automatically modifies the preliminary oxygen saturation level 450 to indicate a hypoxia risk (e.g., oxygen saturation level 450 below acceptable threshold). In still further implementations, if the oxygen sensor 192 indicates a high carbon dioxide and/or nitrogen level, the model 410 automatically modifies the oxygen saturation level 450 to indicate a hypoxia risk (e.g., as inferred by oxygen concentration in the environment being reduced relative to carbon dioxide and/or nitrogen). In additional cases, the model 410 is configured to process inputs from additional sensors 160 independently, such that thresholds for additional sensors 160 are considered separately. In one example, an input from the CO sensor 180 acts as a threshold indicator of a hypoxia (or carbon monoxide poisoning) risk, regardless of an input from another sensor (e.g., oxygen sensor 192). For example, even in scenarios where the oxygen sensor 192 indicates that oxygen concentration in the environment 100 is acceptable (e.g., satisfies or exceeds a threshold), the model 410 can be configured to indicate a hypoxia and/or carbon monoxide poisoning risk (e.g., adjust the oxygen saturation level 450 below acceptable threshold) if the CO sensor 180 indicates the presence of carbon monoxide in the environment 100 satisfies or exceeds a threshold.

Additional sensor modifiers 470 can be based on prompts and/or other interactive data from the additional sensors 160. For example, in certain cases, the wearable device 170 includes one or more of additional sensors 160 for monitoring the user 140 and/or conditions in the environment 100. In a particular example, the wearable device 170 includes a wearable audio device with microphone(s) and at least one electro-acoustic transducer for providing an audio output. In various implementations, the processor 130 is coupled with the microphone and the transducer(s) to control audio functions (among others) at the wearable (audio) device 170. In a particular example, the wearable device 170 includes an aviation headset such as those described in U.S. patent application Ser. No. 16/953,272 (Wearable Audio Device with Control Platform) and U.S. Pat. No. 10,952,668 (Pilot Workload Monitoring System), each of which is incorporated by reference in its entirety. In some cases, the aviation headset is coupled with an electronic flight bag (EFB), which can at least partially contain the processor 130 for performing functions described herein. The example aviation headset can include a set of on-ear, over-ear, near-ear or in-ear earpieces. In a particular example, the aviation headset includes a set of in-ear earpieces. While an aviation headset is described according to some implementations, the headset-type wearable audio device can be useful in various non-aviation environments, e.g., in any high-pressure and/or low-pressure environment such as while hiking, climbing, diving, mining, in an industrial environment such as a food processing facility (e.g., meat-processing), in a clean room or other environmentally sealed facility, etc.

In a particular example such as where the wearable device 170 includes a wearable audio device and is configured to use feedback and/or other interactive data in assessing user health risk, the processor 130 is configured to prompt the user 140 to speak (e.g., via an interface message, audio output from transducer, etc.), receive voice signals from the user 140 after the prompt (e.g., via microphone(s) 198), and identify a potential oxygen saturation level indicator based on the received voice signals. For example, a potential oxygen saturation level indicator can be based on a speech pattern that is indicative of low oxygen saturation level. In additional implementations, the processor 130 is configured to monitor voice signals from the user 140 over a period (e.g., via microphone(s) 198), and identify a potential oxygen saturation level indicator based on the monitored voice signals. In such cases, the logic 210 can include speech pattern data that is specific to the user 140 and/or a group of users, or a speech pattern for a default user or profile. The logic 210 can be configured to detect speech patterns in received acoustic signals (via microphone(s) 198) or via any other voice and/or speech detection system in the additional sensors 160 (e.g., voice activity detection (VAD) system, a system for detecting jaw and/or head movement, etc.) either in response to prompt(s), or within a given monitoring period.

In any case, returning to FIG. 3, the physiology model 410 is configured to provide an oxygen saturation output 430 that can be used as an input to an action decision model 500 for determining whether the oxygen saturation level of the user 140 meets one or more predetermined conditions, and if so, defining an action for the processor 130 to perform. In certain implementations, the action decision model 500 is configured to select a first corrective action (Action 1) for the processor 130 to perform in response to determining that the oxygen saturation level 430 deviates from an oxygen saturation threshold, e.g., a hypoxia danger threshold. An example oxygen saturation threshold (e.g., low blood oxygen threshold) can range from approximately 90 percent oxygen saturation to approximately 95 percent oxygen saturation. In additional implementations, a severe oxygen saturation threshold is defined as an oxygen saturation below approximately 90 percent oxygens saturation. In certain environments, e.g., aviation usage, the oxygen saturation threshold can vary based on altitude. For example, where the monitoring system 110 is part of an aviation system, the oxygen saturation threshold can be set at approximately 90 percent for altitudes up to approximately 10,000 feet (approximately 3,000 meters). In certain cases, the first corrective action includes a notification, e.g., to the user 140 and/or to another user such as a co-pilot, air traffic controller, trip monitoring system, or vehicle control system (e.g., aircraft controller, vehicle controller or underwater vessel controller). In certain cases, the processor 130 provides feedback to the user 140 with a suggestion to take an action that is likely to adjust the oxygen saturation level in response to the oxygen saturation level 430 deviating from the threshold (e.g., notifying a pilot to reduce altitude). In particular examples, the processor 130 is also configured to take follow-up action if a notification is provided and a subsequent oxygen saturation level output 430 indicates an oxygen saturation level that deviates from an oxygen saturation threshold (e.g., oxygen saturation level that is too high, or too low). In certain cases, the processor 130 monitors subsequent oxygen saturation level outputs 430 for a period (e.g., several minutes to an hour) after providing the notification, and takes a follow-up action if the subsequent oxygen saturation level output 430 indicates an oxygen saturation level that deviates from the oxygen saturation threshold and/or is farther from the oxygen saturation threshold than at least one recent prior oxygen saturation level output 430.

In certain implementations, as noted herein, the carbon monoxide measurement (from CO sensor 180) enhances an accuracy of the determined oxygen saturation level output 430 from the model 410. That is, the CO sensor 180 can provide an additional input to the physiology model 410 for indicating a likelihood that the user 140 is experiencing or likely to experience hypoxia. For example, the CO sensor 180 can indicate that the presence of carbon monoxide in environment 100 is likely to cause carbon monoxide-induced hypoxia in the user 140. In particular cases, if the carbon monoxide measurement indicates a carbon monoxide level that satisfies a threshold (e.g., CO threshold, such as that CO-induced hypoxia is potentially occurring), the processor 130 is configured to take a second, distinct corrective action. In some cases, the second type of corrective action can include switching the vehicle control system into an automatic control setting (e.g., autopilot in an airplane, or automatic control in another vehicle), and/or automatically adjusting airflow to/from the environment 100 to reduce the level of CO in the environment 100.

In particular implementations, sensing the presence of CO in the environment 100 can aid in detecting more subtle, or hard-to-detect forms of CO-related health concerns, e.g., CO-induced hypoxia. In contrast to conventional pulse oximeters, the monitoring system 110 can aid in reliably detecting CO-induced hypoxia. That is, this form of CO poisoning can evade conventional pulse oximeters. For example, CO bonds tightly, even preferentially, to hemoglobin, and the CO bonded (or contaminated) hemoglobin has a bright red color very close to well oxygenated blood. Certain conventional pulse oximeters are unable to detect (or unreliably detect) such CO-based contamination, and instead report such contamination as good oxygenation. In contrast, the monitoring system 110 is configured to detect characteristics of both the environment and the user's oxygen saturation level to accurately detect and/or predict CO-based health concerns. Additionally, the monitoring system 110 can provide a comprehensive approach to monitoring aspects of the environment 100 that can induce health concerns for the user 140, e.g., the concentration of nitrogen and/or $CO_2$. The monitoring system 110 can be configured to warn of hypoxia by detecting unusually high levels of non-helpful substances such as nitrogen and/or $CO_2$ (and associated low levels of oxygen) being taken in by the user. These features of the monitoring system 110 can provide significant benefits relative to conventional direct pulse oxygen measurements or air monitoring systems. The monitoring system 110 can provide comprehensive and in many cases predictive indicators of environmental risk to human users in a variety of environments. Even further, implementations of the monitoring system 110 that include sensing or detection of oxygen or other gases (e.g., CO) present in the environment (in addition to determining user oxygen concentration from pressure and other inputs), can add value as a potential early warning to the user 140, and in warning of the nature of the detected problem. For example, these aspects of the monitoring system 110 can beneficially provide indicators to the user 140 and/or others in environments where oxygen is low because pressure is low (e.g., altitude is high), oxygen is low because CO is present and creating CO poisoning, oxygen is low because nitrogen concentration is higher than normal, and/or oxygen is low because $CO_2$ is higher than normal.

While various thresholds are described herein as based on user characteristics that may be general in nature, e.g., a minimum blood oxygen saturation level, or a maximum carbon monoxide level in the environment 100, a number of user characteristics can be provided by the user 140 via one or more interfaces on the smart device 150, wearable device 170 and/or other connected devices (e.g., electronic flight bag and/or flight control system). In certain aspects, user characteristics include predefined settings specific to the user 140 (e.g., an aircraft pilot). For example, an oxygen saturation threshold can be based upon predefined settings that are specific to the pilot of the aircraft. In one example, the user 140 can set and/or adjust predefined user characteristics to his/her comfort level or preferences. The user 140 can define and/or adjust these settings and associated thresholds via a user interface, for example, through an interface connected with the monitoring engine 200, e.g., running on the smart device 150 (FIG. 1). In particular implementations, the user 140 can insert or adjust values for settings using the interface, e.g., by typing, speaking, selecting or otherwise entering a value within a range for a setting, or gesturing, sliding, or dialing between values for a setting. Additional examples of user interfaces, such as those provided to aircraft pilots or other vehicle operators, are included in U.S. Pat. No. 10,952,668, previously incorporated by reference herein.

While thresholds are described in some cases as being specific values, e.g., a value of X or Y, it is understood that thresholds can also include ranges of values. For example, falling below a threshold value for a user characteristic (e.g., blood oxygen saturation level) can be undesirable, but so can exceeding a threshold value for that same user characteristic. In these scenarios, a threshold can include a threshold range or band of values, such that deviation from that threshold is indicated as undesirable. In various implementations, the thresholds used to calculate the workload component can be specific to each user characteristic, aircraft condition and/or physiological condition.

In some cases, the another user 140 can enter the predefined user characteristics into the monitoring engine 200, e.g., as preferences or values within predefined ranges. In additional implementations, the thresholds are based upon a data model defining a physiological fatigue and/or physical danger threshold specific to the user, e.g., a pilot of an aircraft. In some example cases, the data model(s) described herein, e.g., physiology model 410 and/or action decision model 500 are developed via simulations with the pilot, simulations with one or more other pilots, and/or with empirical data gathered from one or more pilots operating in the field. In particular cases, the monitoring engine 200 can use statistical averages, deviations, etc. from a data set obtained from a plurality of pilots and associated flights in order to construct the thresholds. The thresholds are correlated with physiological danger and/or fatigue thresholds for the pilot (or a representative pilot), such that values that meet or deviate from the thresholds (e.g., fall below a lower value or exceed an upper value) can indicate danger of physiological fatigue or more significant health risk to the pilot. For example, an EEG reading detected by a physiological sensor 190 (FIG. 1) that is below a threshold value or range can indicate a pilot health condition (e.g., hypoxia, hypoxia risk, fatigue, etc.). In other examples, a lack of eye movement (e.g., in terms of frequency and/or range of movement) can indicate a pilot health condition. In still further examples, delayed pilot action (also called “getting behind the aircraft”) can indicate a pilot health condition, such as where a pilot is late in making a descent, or reacts to dynamic conditions in a time greater than a desired period (e.g., as derived from an average of a data set, or an industry standard time). This delayed pilot action can be detected using any of the additional sensors 160, e.g., by pilot movement detected using the IMU 194, optical sensor 196, etc., and/or altitude sensors for detecting delays in ascent/descent. In a particular example, a standard descent threshold can be X feet/min (e.g., 1,000 ft/min), and significant deviation from this threshold can be used as a factor to indicate a pilot health condition. In another example, historical data such as GPS/location data from other aircraft making a similar approach can be used to define the data model. In these cases, the monitoring engine 200 can use a threshold descent rate that is specific to a particular airport or location in evaluating pilot health conditions. These additional thresholds can be used to inform potential corrective actions for the pilot and/or provide information about how other factors impact blood oxygen saturation levels.

In multi-component calculations factoring in blood oxygen saturation level, fatigue and/or other dangers to the pilot, the value of a component (e.g., pressure oxygen level, IMU-based activity, voice feedback, etc.) can dictate the weighting assigned to that component, such as where a higher (or lower) value is assigned a greater weighting. In various implementations, the higher the value of the component (indicating undesirable deviation from the threshold or threshold range), the greater the weight that is applied to that component. This can enhance the significance of conditions that deviate from the threshold (range).

In certain additional implementations, the monitoring engine 200 is configured to compile data from the pressure sensor(s) 120, additional sensors 160, and outputs from models 410 and 500 and output that data in a report indicating physiological conditions and/or environmental conditions for the user 140 over a period or a trip. In various implementations, the report includes one or more of: an in-trip indicator of the physiological conditions and/or the environment conditions for the user 140 during a trip or period (e.g., during a flight), a predictive indicator of the physiological conditions and/or the environment conditions for the user 140 at a future time, or a post-trip (e.g., post-flight) report of the physiological conditions and/or the environment conditions for the user 140 during the trip. In additional implementations, the report includes suggested adjustments to at least one aircraft configuration metric, user behavior, etc. to reduce the risk of physiological and/or environmental danger for the user (e.g., pilot). For example, an in-flight report can include suggestions (presented in text or audio form) such as: “Consider dimming the cockpit lights to reduce stress on your eyes.” An example pre-flight report can include suggestions such as: “Consider alternate flight pattern to reduce time of flight.” An example post-flight report can include notes such as: “The turbulence encountered at Location X increased your stress level by 20%; adjusting altitude and/or path prior to Location X would have mitigated this stress.” Another example post-flight report can include suggestions such as: “Consider aircraft (or other vessel) inspection and/or maintenance due to detected presence of carbon monoxide during trip.

In certain cases, the projected conditions can also be based (in part) upon the data model defining physiological fatigue thresholds and/or other health conditions for the user(s), e.g., relying upon historical data from the user or other users to project a future condition, given the user’s current and past condition(s), rates of change, and deviations from one or more thresholds.

In the case that the user 140 is a pilot such as an aircraft pilot or a vehicle operator, the smart device 150 can be integrated within, or otherwise connected with, a flight (or trip) management system coupled with a network of sensors, both inside the cabin (e.g., in the environment 100) as well as external to the cabin (and in some cases, external to the aircraft). These sensors can include temperature sensors, pressure sensors, humidity sensors, light sensors, wind sensors, etc. The flight management system is configured to maintain (e.g., receive or otherwise gather) flight condition data from the sensors as well as the communications system. In some examples, flight condition data can include data about one or more of: a weather condition proximate the aircraft flown by the user 140 during flight, an altitude of the aircraft during flight, a wind condition proximate the aircraft during flight, a deviation of the aircraft from a planned route, surrounding aircraft position data (e.g., including proximity, routes, density, etc.), an amount of turbulence experienced by the aircraft during flight, a total flight time for the aircraft, a distance traveled by the aircraft during flight, or an ambient lighting condition proximate the aircraft during flight.

In various implementations, the smart device 150 is connected with at least one of the headset wearable device 170, the pressure sensor 120, the additional sensors 160 or the flight management system, and is configured to monitor health conditions for the pilot as well as environmental conditions in the cabin using data from one or more of these connected systems. In various implementations, the smart device 150 is connected with each of the headset wearable device 170, the pressure sensor 120, the additional sensors 160 and the flight management system.

The oxygen saturation management engine 200 shown and described herein can be configured to provide real-time, predictive and post-trip analysis of conditions and configurations that can impact user health and safety, for example, contributing to user (e.g., pilot) fatigue and/or significant adverse health conditions. In contrast to conventional approaches that utilize invasive, unwieldy and/or power-hungry components, the approaches described herein perform accurate and reliable modeling of environmental conditions and other user health risk factors based on input from one or more pressure sensors. Additionally, the approaches described herein can effectively detect and/or predict carbon monoxide-induced hypoxia and other significant adverse health conditions.

The systems and methods described herein can improve situational awareness, fatigue mitigation, and/or navigation for a vehicle operator, e.g., an aircraft pilot. These systems and methods may aid in complying with Federal Aviation Administration (FAA) requirements for flight limitations and rest requirements, as described in 14 C.F.R. § 117.

The functionality described herein, or portions thereof, and its various modifications (hereinafter "the functions") can be implemented, at least in part, via a computer program product, e.g., a computer program tangibly embodied in an information carrier, such as one or more non-transitory machine-readable media, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing all or part of the functions can be performed by one or more programmable processors executing one or more computer programs to perform the functions of the calibration process. All or part of the functions can be implemented as, special purpose logic circuitry, e.g., an FPGA and/or an ASIC (application-specific integrated circuit). Processors suitable for the execution of a computer program include, by way of example, both general and special purpose microprocessors, and any one or more processors of any kind of digital computer. Generally, a processor will receive instructions and data from a read-only memory or a random access memory or both. Components of a computer include a processor for executing instructions and one or more memory devices for storing instructions and data.

Other embodiments and applications not specifically described herein are also within the scope of the following claims. For example, a headset in accordance with the technology described herein may be configured to receive a phone call while in P2P communication mode. For example, if one of the users communicating over a P2P mode receives a phone call, the corresponding headset can be configured to suspend the P2P communication link temporarily to allow the user to have a private phone call. In such cases, another module (e.g., a Bluetooth® module communicating with a phone) of the headset may be activated upon suspension of the P2P link. In some implementations, the P2P mode may automatically be resumed or reinstated upon termination of the phone call. Elements of different implementations described herein may be combined to form other embodiments not specifically set forth above. Elements may be left out of the structures described herein without adversely affecting their operation. Furthermore, various separate elements may be combined into one or more individual elements to perform the functions described herein.

In various implementations, components described as being "coupled" or "connected" to one another can be joined along one or more interfaces. In some implementations, these interfaces can include junctions between distinct components, and in other cases, these interfaces can include a solidly and/or integrally formed interconnection. That is, in some cases, components that are "coupled" or "connected" to one another can be simultaneously formed to define a single continuous member. However, in other implementations, these coupled components can be formed as separate members and be subsequently joined through known processes (e.g., soldering, fastening, ultrasonic welding, bonding). In various implementations, electronic components described as being "coupled" or "connected" can be linked via conventional hard-wired and/or wireless means such that these electronic components can communicate data with one another. Additionally, sub-components within a given component can be considered to be linked via conventional pathways, which may not necessarily be illustrated.

A number of implementations have been described. Nevertheless, it will be understood that additional modifications may be made without departing from the scope of the inventive concepts described herein, and, accordingly, other embodiments are within the scope of the following claims.

We claim:

1. A monitoring system, comprising:

at least one pressure sensor for detecting air pressure in an environment proximate the at least one pressure sensor;

at least one additional sensor distinct from the at least one pressure sensor; and a processor coupled with the at least one pressure sensor and the at least one additional sensor, wherein the processor is programmed to receive air pressure data from the pressure sensor about the environment, determine an oxygen saturation level for a user in the environment based on the air pressure data, wherein the oxygen saturation level is determined using a physiology model having:

an oxygen saturation level correspondence with air pressure data, and a sensitivity modifier for modifying a sensitivity of the physiology model in calculating the oxygen saturation level based on at least one measurement or determined input from the at least one additional sensor deviating from a threshold, wherein the sensitivity modifier is configured to adjust a sensitivity to a preliminary oxygen saturation level that deviates from an oxygen saturation level threshold in response to an air pressure value, as detected by the at least one pressure sensor or the at least one additional sensor, either: exceeding a high pressure threshold, or being below a low pressure threshold, and in response to determining the oxygen saturation level of the user has met one or more predetermined conditions, perform an action.

2. The system of claim 1, wherein the physiology model further includes an oxygen saturation level correspondence with user characteristics, wherein each user characteristic has at least two values, each of the at least two values being associated with a distinct weight to be applied to the air pressure data, and wherein determining the oxygen saturation level includes:

applying a first weight to the air pressure data based on a first value for a first user characteristic, and applying a second weight to the air pressure data based on a second value for the first user characteristic, wherein the first weighted air pressure data results in a first determined oxygen saturation level and the second weighted air pressure data results in a second determined oxygen saturation level, wherein the first user characteristic includes gender, and the first value is a default gender value.

3. The system of claim 1, wherein the at least one additional sensor includes a carbon monoxide sensor coupled with the processor for providing a carbon monoxide measurement about the environment, wherein one of the predetermined conditions includes determining that the oxygen saturation level deviates from an oxygen saturation threshold, and wherein the processor is further configured to take a first corrective action, and wherein the carbon monoxide measurement enhances an accuracy of the determined oxygen saturation level, wherein if the carbon monoxide measurement indicates a carbon monoxide level exceeding a threshold, the processor is further configured to take a second, distinct corrective action.

4. The system of claim 1, wherein the processor is further programmed to provide a notification to the user to select at least one individual user characteristic prior to determining an oxygen saturation level for the user, wherein the notification indicates that the at least one individual user characteristic enhances accuracy in determining the oxygen saturation level for the user.

5. The system of claim 1, wherein the processor is further programmed to determine the oxygen saturation level based on at least one user characteristic, wherein the at least one user characteristic includes one or more of: gender, resting heart rate, age, weight, resting respiration rate, or baseline blood pressure.

6. The system of claim 5, wherein:

a) the at least one user characteristic is selected by the user, b) all of the user characteristics are default user characteristics, or c) at least one user characteristic is received from a physiological sensor in the environment.

7. The system of claim 6, wherein the at least one user characteristic is received from the physiological sensor, the system further comprising:

a wearable audio device coupled with the processor, wherein the wearable audio device includes the physiological sensor.

8. The system of claim 6, wherein the at least one user characteristic is received from the physiological sensor, wherein the physiological sensor includes an optical sensor for providing eye movement data for use by an action decision model.

9. The system of claim 1, wherein the oxygen saturation level includes at least one of an arterial blood gas level or a pulse oxygen level.

10. The system of claim 1, wherein the at least one additional sensor includes one or more of: an oxygen sensor, a carbon monoxide sensor, an inertial measurement unit, an optical sensor, or a microphone, wherein the at least one additional sensor includes a set of redundant sensors at physically distinct devices.

11. The system of claim 1, further comprising:

a wearable audio device coupled with the processor, wherein the wearable audio device includes at least one electro-acoustic transducer for providing an audio output and at least one microphone, wherein the processor is configured to, prompt the user to speak, receive voice signals from the user after the prompt, and identify a potential oxygen saturation level indicator based on the received voice signals, or monitor voice signals from the user over a period, and identify a potential oxygen saturation level indicator based on the monitored voice signals.

12. The system of claim 11, wherein the user is an aircraft pilot and the wearable audio device comprises an aviation headset, and wherein the processor is at least partially contained in the wearable audio device or an electronic flight bag coupled with the wearable audio device, wherein the wearable audio device comprises a set of in-ear earpieces.

13. The system of claim 1, further comprising an oxygen sensor coupled with the processor for providing an indicator of at least one of an oxygen level or a nitrogen level in the environment.

14. The system of claim 1, wherein the processor is further configured to:

provide feedback to the user to adjust the determined oxygen saturation level in response to the determined oxygen saturation level deviating from a threshold.

15. The system of claim 1, wherein the action comprises at least one of: providing feedback to the user about one of the predetermined conditions, alerting another user about one of the predetermined conditions, or automatically taking a corrective action.

16. The system of claim 1, wherein the sensitivity modifier is based on an environmental gaseous mixture characteristic including at least one of: detected air pressure, altitude, a carbon monoxide value, or a nitrogen value, and aids in detecting carbon monoxide (CO) induced hypoxia in the user in an airplane cabin.

17. The system of claim 1, wherein the at least one additional sensor includes an altitude sensor, and wherein in response to an input from the altitude sensor exceeding a high altitude threshold, the sensitivity modifier is configured to be applied to increase a sensitivity of the physiology model to a preliminary oxygen saturation level that deviates from an oxygen saturation threshold.

18. The system of claim 1, wherein the physiology model is configured to determine a preliminary oxygen saturation level, and further includes an additional sensor modifier configured to act as a threshold to trigger an adjustment to the determined preliminary oxygen saturation level.

19. The system of claim 18, wherein the at least one additional sensor includes an oxygen sensor, wherein:

a) if the oxygen sensor indicates a low oxygen environment, the additional sensor modifier is configured to automatically modify the preliminary oxygen saturation level to indicate a hypoxia risk, or b) if the oxygen sensor indicates a high carbon dioxide level and/or high nitrogen level, the additional sensor modifier is configured to automatically modify the preliminary oxygen saturation level to indicate a hypoxia risk.

20. A method of monitoring an oxygen saturation level of a user, the method comprising:

receiving air pressure data from at least one pressure sensor about an environment proximate the at least one pressure sensor, receiving at least one measurement or determined input from at least one additional sensor distinct from the at least one pressure sensor, wherein the at least one additional sensor includes an oxygen sensor, determining an oxygen saturation level for the user in the environment based on the air pressure data, wherein the oxygen saturation level is determined using a physiology model having:

an oxygen saturation level correspondence with air pressure data, and a sensitivity modifier for modifying a sensitivity of the physiology model in calculating the oxygen saturation level based on the at least one measurement or determined input from the at least one additional sensor deviating from a threshold, wherein the physiology model is configured to determine a preliminary oxygen saturation level, and further includes an additional sensor modifier configured to act as a threshold to trigger an adjustment to the determined preliminary oxygen saturation level, wherein:

a) if the oxygen sensor indicates a low oxygen environment, the additional sensor modifier is configured to automatically modify the preliminary oxygen saturation level to indicate a hypoxia risk, or b) if the oxygen sensor indicates a high carbon dioxide level and/or high nitrogen level, the additional sensor modifier is configured to automatically modify the preliminary oxygen saturation level to indicate a hypoxia risk, and in response to determining the oxygen saturation level of the user has met one or more predetermined conditions, performing an action.

21. The method of claim 20, wherein the physiology model has a variable sensitivity based on an environmental gaseous mixture characteristic as detected by the at least one additional sensor.

22. The method of claim 20, wherein the physiology model further includes an oxygen saturation level correspondence with user characteristics, and wherein determining the oxygen saturation level includes:

applying a first weight to the air pressure data based on a first value for a first user characteristic, and applying a second weight to the air pressure data based on a second value for the first user characteristic, wherein the first weighted air pressure data results in a first determined oxygen saturation level and the second weighted air pressure data results in a second determined oxygen saturation level, wherein the first user characteristic includes gender, and the first value is a default gender value.

23. The method of claim 20, wherein one of the predetermined conditions includes determining that the oxygen saturation level deviates from an oxygen saturation threshold, wherein the action includes a first corrective action.

24. A monitoring system, comprising:

at least one pressure sensor for detecting air pressure in an environment proximate the at least one pressure sensor;

at least one additional sensor distinct from the at least one pressure sensor, wherein the at least one additional sensor includes a carbon monoxide sensor for providing a carbon monoxide measurement about the environment; and a processor coupled with the at least one pressure sensor and the at least one additional sensor, wherein the processor is programmed to receive air pressure data from the pressure sensor about the environment, determine an oxygen saturation level for a user in the environment based on the air pressure data, wherein the oxygen saturation level is determined using a physiology model having:

an oxygen saturation level correspondence with air pressure data, and a sensitivity modifier for modifying a sensitivity of the physiology model in calculating the oxygen saturation level based on at least one measurement or determined input from the at least one additional sensor deviating from a threshold, and in response to determining the oxygen saturation level of the user has met one or more predetermined conditions, perform an action, wherein one of the predetermined conditions includes determining that the oxygen saturation level deviates from an oxygen saturation threshold, and wherein the processor is further configured to take a first corrective action, wherein if the carbon monoxide measurement indicates a carbon monoxide level exceeding a threshold, the processor is further configured to take a second, distinct corrective action, and wherein the carbon monoxide measurement enhances an accuracy of the determined oxygen saturation level.

25. The monitoring system of claim 24, wherein the oxygen saturation level includes at least one of an arterial blood gas level or a pulse oxygen level.

* * * * *